United States Patent
Liu et al.

(10) Patent No.: US 10,123,762 B2
(45) Date of Patent: Nov. 13, 2018

(54) SYSTEM AND METHOD FOR ADJUSTING DENTAL X-RAY EXPOSURE

(71) Applicant: BAE Systems Imaging Solutions Inc., San Jose, CA (US)

(72) Inventors: Xinqiao Liu, Mountain View, CA (US); Boyd Fowler, Sunnyvale, CA (US)

(73) Assignee: BAE Systems Imaging Solutions Inc., San Jose, CA (US)

( * ) Notice: Subject to any disclaimer, the term of this patent is extended or adjusted under 35 U.S.C. 154(b) by 285 days.

(21) Appl. No.: 14/988,623

(22) Filed: Jan. 5, 2016

(65) Prior Publication Data
US 2017/0188987 A1    Jul. 6, 2017

(51) Int. Cl.
*A61B 6/00* (2006.01)
*A61B 6/14* (2006.01)
*G01T 1/02* (2006.01)

(52) U.S. Cl.
CPC .............. *A61B 6/542* (2013.01); *A61B 6/145* (2013.01); *A61B 6/4266* (2013.01); *A61B 6/56* (2013.01); *G01T 1/02* (2013.01)

(58) Field of Classification Search
CPC .................................................... A61B 6/145
See application file for complete search history.

(56) References Cited

U.S. PATENT DOCUMENTS

| 6,404,854 B1 | 6/2002 | Carroll et al. |
| 2006/0008050 A1* | 1/2006 | Massie ................. A61B 5/0088 378/38 |
| 2011/0249792 A1 | 10/2011 | Lalena et al. |
| 2012/0093295 A1* | 4/2012 | Newman .............. A61B 6/4233 378/114 |

OTHER PUBLICATIONS

International Search Report, PCT/US2017/018658, dated May 4, 2017, 16 pages.

* cited by examiner

*Primary Examiner* — Dani Fox
(74) *Attorney, Agent, or Firm* — Calvin B. Ward

(57) ABSTRACT

An x-ray imaging system and a method for retrofitting existing x-ray generators to allow those generators to be controlled by a digital x-ray imaging system are disclosed. The x-ray imaging system includes an imaging array and an image controller. The imaging array is configured to be positioned within a patient's mouth, the imaging array acquiring an image of the patient's teeth when the patient's head is illuminated with x-rays. The imaging array includes an x-ray dosimeter that provides an x-ray exposure signal indicative of an x-ray exposure received by the imaging array. The image controller is coupled to the imaging array and receives the x-ray exposure signal, the image controller includes a first wireless link that controls an x-ray generator by initiating a pre-programmed x-ray exposure. The wireless controllable switch can be used to replace an existing manually controlled switch in an existing x-ray generator.

8 Claims, 3 Drawing Sheets

SYSTEM AND METHOD FOR ADJUSTING DENTAL X-RAY EXPOSURE

BACKGROUND

X-ray imaging is commonly used as a diagnostic tool in dental settings. Traditionally, film was used as the x-ray detector. The film is inserted into the patient's mouth behind the teeth and the outside of the patient's jaw is exposed to a pulse of x-rays. The teeth absorb the x-rays, and hence, create contact images of the teeth on the film which are then used by the dentist to diagnose the state of the teeth.

This system had a number of problems that have been overcome to some degree by replacing the film with a digital image sensor. In such systems, a scintillator is used to convert the x-rays to visible light. The light is collimated by a fiber optic bundle, and a CMOS image sensor of substantially the same type as used in digital photography is used to detect the generated light that leaves the collimator.

The time and cost of processing the film are substantial in a film-based system. Converting the film images to digital form for storage in a modern record keeping system further increases the cost of such systems both in terms of equipment and operator time. Digital image sensors avoid the film processing and provide a final image that is in a form compatible with digital record storage systems.

Determining the correct exposure presents problems with film which are partially solved by the use of digital sensors. The dynamic range of the film is typically less than a factor of 100. That is, the ratio of the highest light level that can be recorded without saturating the film to the lowest level that can be detected is of the order of 100. This dynamic range is sufficient to provide useable images if the exposure is correctly set. However, setting the exposure presents challenges. If too short of an x-ray exposure is used, the image will lack detail in the darker areas. If the x-ray exposure is too high, part of the image will be overexposed and insufficient detail will be present. The correct exposure, in general, depends to some degree on the structure of the patient's face, as the patient's face absorbs part of the x-ray before the x-rays reach the teeth.

Digital sensors have substantially higher dynamic ranges than film. Hence, even if the exposure is above or below the optimum level needed to place the image in the linear range of the sensor response function, a useable image can be obtained by digitally processing the image. However, providing an optimal exposure is still advantageous.

Digital sensors also require substantially less x-ray exposure to form a usable image. In general, it is advantageous to reduce the x-ray exposure to which the patient is subjected to as low a level as possible. Hence, digital sensors hold the promise of reducing this exposure. However, this promise has only partially been achieved by current digital x-ray systems.

In general, the x-ray generating system is independent from the imaging sensor. For example, a dentist who desires to switch from film to a digital sensor, typically uses the dentist's existing x-ray system and merely reduces the exposure to a level that provides satisfactory images. The technician places the digital sensor in the patient's mouth and then triggers the x-ray system to provide a pulse of x-rays that is sufficient to provide the desired image. The digital sensor sends the image to a computer that processes the image and stores the data in the electronic patient information system.

Systems in which the digital sensor detects the start of the x-ray pulse and begins its exposure when the pulse is detected have been suggested. Such systems can also end the exposure when sufficient x-rays have been detected by the same sensor mechanism. However, these systems do not have any mechanism for turning off the x-ray generator when there is sufficient data to form an image, and hence, the patient is subjected to additional x-ray exposure that provides no therapeutic benefit.

Schemes in which a radiation detector associated with the imaging array measures the x-ray dose during the exposure and then turns off the high-voltage supply to the x-ray generator have also been suggested. These systems require an x-ray generator in which the high-voltage can be controlled by the electronics that monitor the exposure measuring device and/or the imaging system. However, most dental offices utilize x-ray systems that were designed for film-based x-ray imaging and do not provide the remote control system required by such automatic exposure systems. In these legacy systems, the operator initiates an exposure of a predetermined length by pressing a button. To protect the operator from repeated exposures, the button is placed at a remote location relative to the patient and x-ray head. In addition, the electronics that control the x-ray exposure do not present a readily accessible location that can be used to fashion a remote control interface that can be used by automatic exposure control systems.

SUMMARY

The present invention includes an x-ray imaging system and a method for retrofitting existing x-ray generators to allow those generators to be controlled by a digital x-ray imaging system. The x-ray imaging system includes an imaging array and an image controller. The imaging array is configured to be positioned within a patient's mouth, the imaging array acquiring an image of the patient's teeth when the patient's head is illuminated with x-rays. The imaging array includes an x-ray dosimeter that provides an x-ray exposure signal indicative of an x-ray exposure received by the imaging array. The image controller is coupled to the imaging array and receives the x-ray exposure signal, the image controller includes a first wireless link that controls an x-ray generator by initiating a pre-programmed x-ray exposure.

In one aspect of the invention, the pre-programmed x-ray exposure is less than the minimum x-ray exposure needed to provide a satisfactory image of the patient's teeth. The image controller repeatedly initiates the pre-programmed x-ray exposure until the exposures taken together provide a satisfactory image of the patient's teeth.

In another aspect of the invention, the image controller includes a second wireless link that interrupts the pre-programmed x-ray exposure. The image controller interrupting the pre-programmed x-ray exposure in response to the x-ray exposure signal indicating that an exposure sufficient to provide a satisfactory image of the patient's teeth had been received.

In a still further aspect of the invention, the image controller is manufactured by a first commercial entity and the system includes an x-ray generator manufactured by a second commercial entity that is different from the first commercial entity, the x-ray generator is sold separately as a stand alone unit for x-ray imaging. The first wireless link communicates with a wireless controlled switch in the x-ray generator, the wireless controlled switch replacing a manually controlled switch in the stand alone unit that initiates x-ray generation.

In another aspect of the invention, the second wireless link controls a wireless controlled switch that interrupts the generation of x-rays by the x-ray generator. The second wireless link interrupts a power line that supplies power to an x-ray generating tube in the x-ray generator.

DETAILED DESCRIPTION

Figure 1:
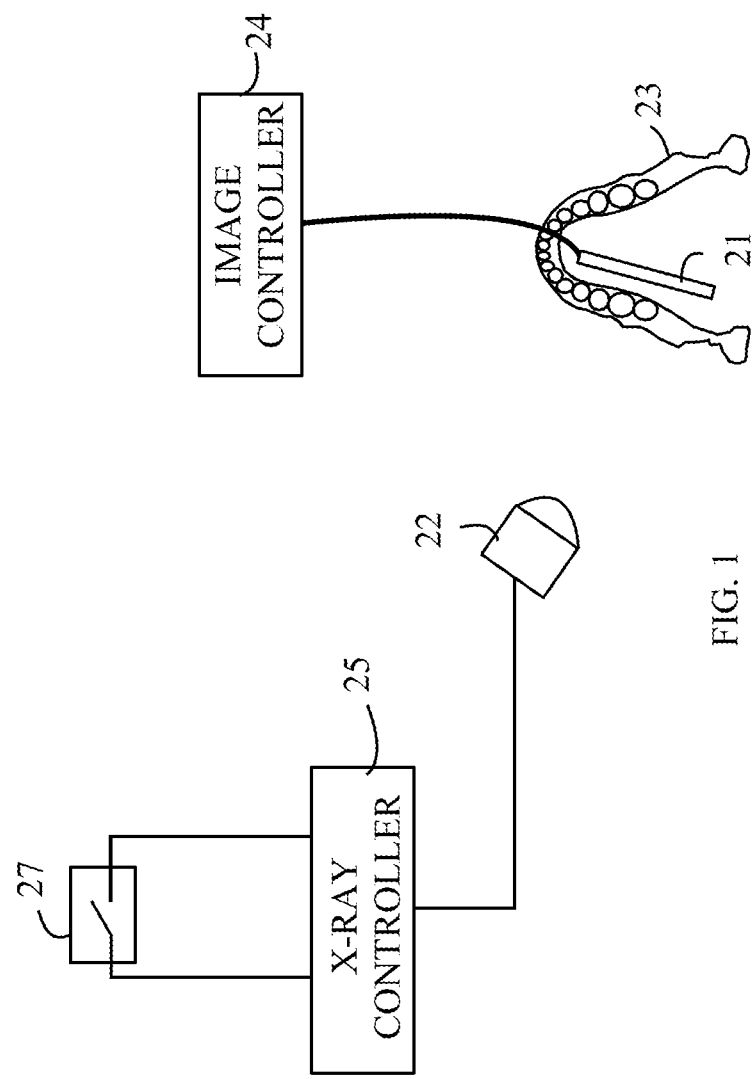
FIG. 1 illustrates the arrangement of the various components in a dental x-ray analysis of a patient's teeth.

The manner in which the present invention provides its advantages can be more easily understood with reference to FIG. 1, which illustrates the arrangement of the various components in a dental x-ray analysis of a patient's teeth. Typically, an imaging sensor 21 is placed in the patient's mouth so that x-rays from an x-ray source 22 will pass through the patient's teeth 23 and be detected by the imaging array. The imaging array is controlled by image controller 24 that processes the data from imaging sensor 21 to provide an image of the patient's teeth that is stored in an electronic file associated with the patient. X-ray source 22 is controlled from a separate X-ray controller 25 that includes a high voltage power supply that applies an acceleration potential that cause electrons to strike a metal target to generate the x-rays. In many dental settings, the x-ray source was purchased by the dentist to be used in a film-based diagnostic system. The digital imaging system is typically purchased as a replacement for the film component of the old x-ray system and is completely independent of the older x-ray source.

In this film replacement mode, the old x-ray system is operated by manually closing a switch 27 that initiates a high voltage pulse of the appropriate length to provide the desired x-ray exposure. Prior art systems in which imaging sensor 21 is controlled in response to the generation of x-rays are known. In such systems, the imaging array is placed in a ready state prior to switch 27 being closed by an operator entering the appropriate command to image controller 24. In these systems, imaging sensor 21 includes a dose measuring sub-system that detects the start of the x-ray pulse. Systems based on measuring currents generated in the imaging sensor itself or a secondary sensor associated with imaging sensor 21 are known to the art. In these systems, the imaging array is reset at the start of the x-ray pulse. The image is accumulated until the x-ray source is turned off. The imaging array can either detect the cessation of the x-ray exposure using the same system that detected the start of the pulse of x-rays or merely wait a predetermined length of time. In either case, the image is readout and processed after the x-ray exposure has been completed.

In this type of system, the x-ray exposure is determined by the settings on the x-ray controller. The settings are typically not varied to account for different patients' facial absorption of the x-rays, etc. As a result, the settings are typically set to some safe setting that ensures a sufficient exposure for all patients. Accordingly, many patients receive a larger exposure than necessary.

Figure 2:
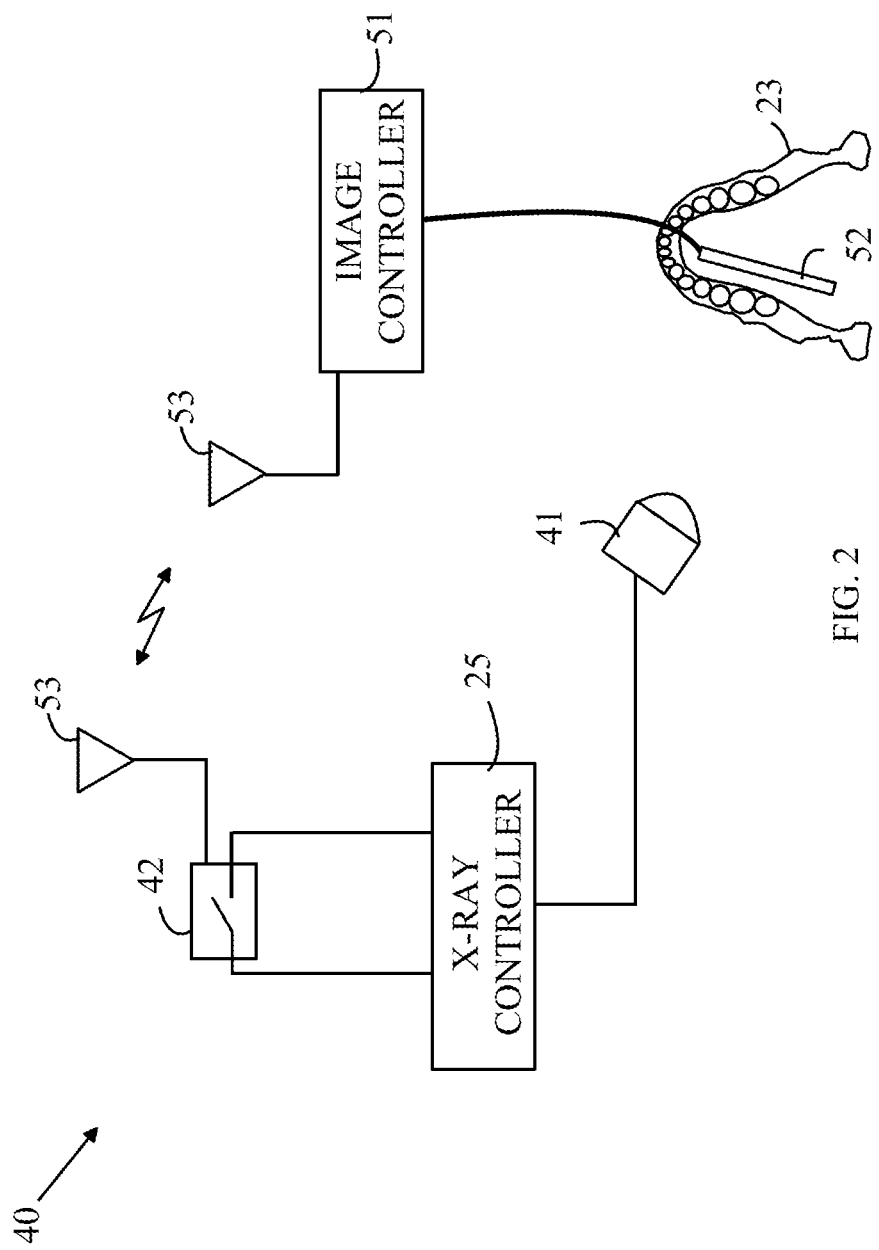
FIG. 2 illustrates one embodiment of an x-ray exposure system according to the present invention.

The present invention overcomes these problems by retrofitting the conventional x-ray system with a trigger switch that can be controlled by the controller that monitors the imaging array and by executing an exposure that consists of a sequence of short pulses of x-rays rather than one long pulse. Refer now to FIG. 2, which illustrates one embodiment of an x-ray exposure system according to the present invention. In digital x-ray system 40, the trigger switch that initiated an x-ray burst from x-ray head 41 has been replaced by a remote controllable switch 42. Since the location of remote controllable switch 42 is not necessarily close to image controller 51 that controls imaging array 52, remote controllable switch 42 preferably communicates with image controller 51 via a wireless communication link 53 such that a cable is not needed between remote controllable switch 42 and image controller 51. Remote controllable switch 42 allows image controller 51 to trigger a pulse of x-rays.

Imaging array 52 includes an x-ray dose detector that measures the dose of x-rays received at imaging array 52. Any of a number of systems for measuring the x-ray dose can be utilized. For example, x-rays striking the imaging array are known to give rise to currents that can be measured. For example, in one a guard ring that is normally used to shield the imaging array from transients generated by other circuitry in a CMOS imaging array is used as an x-ray detector by measuring the current that flows between that guard ring and a power rail. In another example, the imaging array is readout after each pulse of x-rays and the total sub-exposure determined by examining the sums of the signals from a predetermined set of pixels.

As noted above, the x-ray source is operated in a series of shot pulses. In general, the exposure of each pulse is set by controls on the x-ray source. In the present invention, these controls are set such that the pulse delivered in response to each trigger pulse is a small fraction of the required dose to provide an image of the desired quality. For example, each pulse could be set to one-tenth of the expected dose, so that a total of about ten pulses are needed to provide the exposure. In embodiments in which a separate dosimeter is used, image controller 51 initializes imaging array 52 and sends the first pulse of x-rays. Image controller 51 then reads out the dosimeter and determines the number of pulses that will be needed to provide the correct exposure. Image controller 51 then pulses the x-ray source for the determined number of pulses. In one aspect of the invention, image controller 51 reads out the dosimeter at one or more intermediate points in the exposure to verify that the initial estimate of desired exposure time was correct.

In another embodiment, the x-ray dose is set to a small fraction of the estimated correct dose and the dosimeter is readout. Image controller 51 then instructs the operator to set the x-ray exposure to a value determined by that dose. The imaging array is then reset and the x-ray system triggered for the calculated exposure time. This embodiment eliminates the dead time between x-ray pulses; however, it requires more skill and time on the part of the operator.

The remote controllable trigger switch of the present invention provides a simple method for upgrading a conventional x-ray source for use with the digital x-ray system. The switch typically makes a connection between two contacts that are held at a potential relative to one another. This potential difference can be tapped to power the radio link between the remote controllable switch and the controller of the digital x-ray system. If the power available from this source is insufficient, a battery that is charged from the source over a long period of time can be utilized to power the wireless link.

Figure 3:
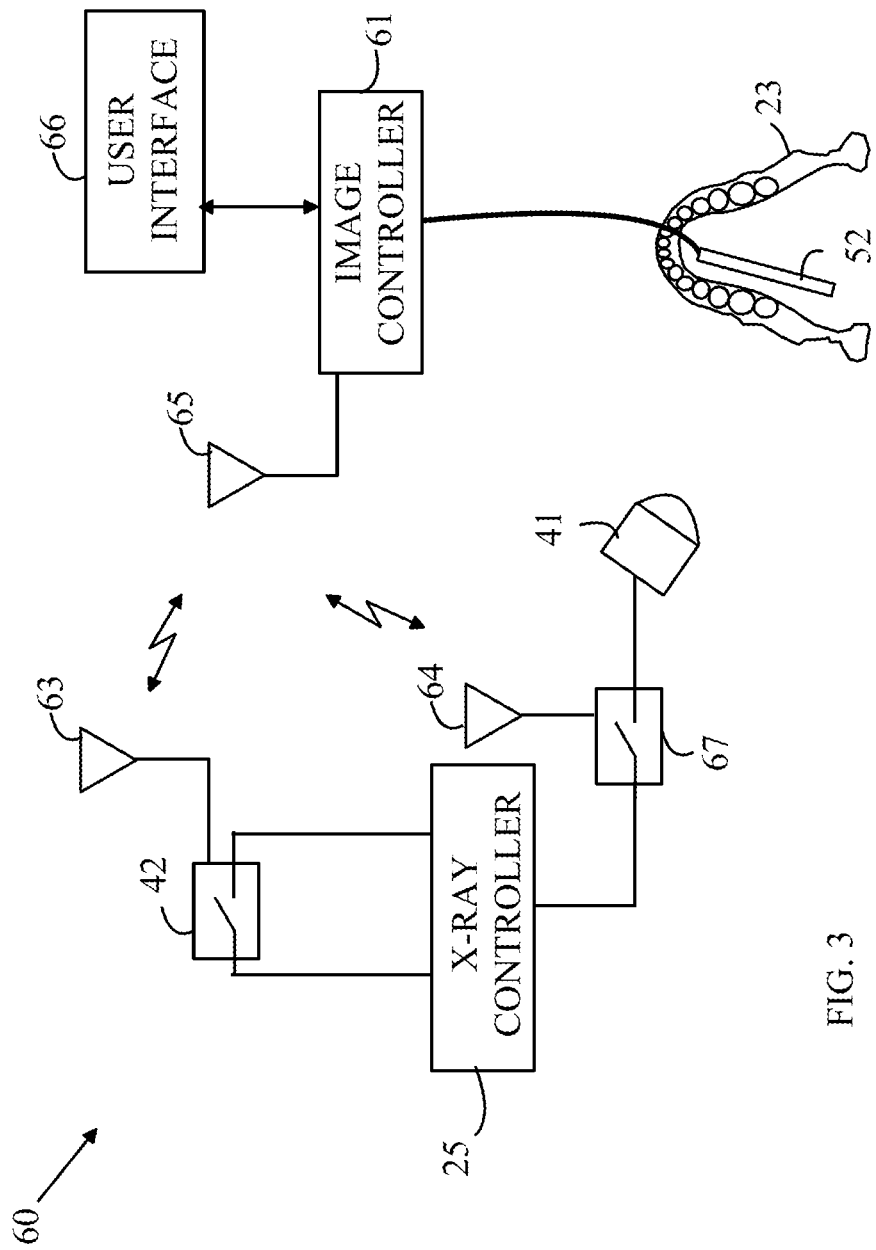
FIG. 3 illustrates another embodiment of a digital x-ray system according to the present invention.

In the above-described embodiments, the radio controllable switch that provides the link between the image controller and the x-ray controller is inserted into the x-ray controller by replacing the x-ray trigger switch that is commonly used in existing x-ray generating systems. Since the trigger switch does not set the length of the x-ray pulse, some other strategy is needed to turn off the x-ray generator when the patient has received the desired level of exposure. In one aspect of the invention, a second radio controlled switch is inserted within the x-ray generation system to interrupt the high voltage to the x-ray head. This second switch allows the imaging controller to terminate the exposure at the appropriate time without significantly altering the underlying electronics of the x-ray generation system. Refer now to FIG. 3, which illustrates another embodiment of a digital x-ray system according to the present invention. To simplify the following discussion, those elements of digital x-ray system 60 that serve functions analogous to elements of digital x-ray system 40 discussed above have been given the same numerical designations as the elements of digital x-ray system 40 and will not be discussed in detail here.

Digital x-ray system 60 is based on the observation that x-ray head 41 typically includes an x-ray generating tube that is powered by a signal source that causes electrons to be accelerated into a metal target. The signal source typically includes a high voltage power supply line that provides the potential for the acceleration. Hence, the x-ray output can be terminated by interrupting this high voltage power line using a second radio remote controlled switch 67 that is operated by a second wireless link 64. In this embodiment, image controller 61 controls the x-ray process and provides the user interface for the control of that process. The x-ray controller 25 is set to provide an exposure that is sufficient to ensure that all patients can receive at least the desired x-ray illumination if the entire exposure is allowed to proceed. When the x-ray imaging process is triggered by a user inputting an appropriate command to image controller 61 via user interface 66, image controller 61 uses the wireless interface between antennas 63 and 65 to trigger the x-ray generator with wireless link 64 closed. After image controller 61 detects that the desired x-ray exposure has been obtained, image controller 61 opens radio remote controlled switch 67 using the wireless link between wireless link 64 and antenna 65. The remainder of the programmed exposure in x-ray controller 25 does not generate x-rays.

The above-described embodiments of the present invention can be advantageously used in dental settings having existing x-ray generators. Typically, these x-ray generators are made by a different manufacturer or commercial entity than the manufacturer of the digital image controller. The present invention provides a method for slaving the x-ray generator to the digital imaging system that requires only minimal changes to the x-ray generator. These changes can be provided on site in a dental office that already has an x-ray generator or by the manufacturer of digital x-ray imaging system that then sells a complete system to the dentist.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. An x-ray imaging system comprising:
    an imaging array configured to be positioned within a patient's mouth, said imaging array acquiring an image of said patient's teeth when said patient's head is illuminated with x-rays from an x-ray generator that is fixed with respect to the patient's teeth and said imaging array, said imaging array comprising an x-ray dosimeter that provides an x-ray exposure signal indicative of an x-ray exposure received by said imaging array; and
    an image controller that is coupled to said imaging array and receives said x-ray exposure signal, said image controller comprising a first wireless link that controls said x-ray generator by initiating a pre-programmed x-ray exposure via said first wireless link, said image controller further comprises a second wireless link that interrupts said pre-programmed x-ray exposure, said image controller interrupting said pre-programmed x-ray exposure in response to said x-ray exposure signal indicating that an exposure sufficient to provide a satisfactory image of said patient's teeth had been received.

2. The x-ray imaging system of claim 1 wherein said pre-programmed x-ray exposure is less than the minimum x-ray exposure needed to provide a satisfactory image of said patient's teeth and wherein said image controller repeatedly initiates said pre-programmed x-ray exposure without moving said x-ray generator or said imaging array until said exposures taken together provide said satisfactory image of said patient's teeth as measured by said x-ray dosimeter.

3. The x-ray imaging system of claim 1 wherein said image controller is manufactured by a first commercial entity and said system includes said x-ray generator manufactured by a second commercial entity that is different from said first commercial entity, said x-ray generator being sold separately as a stand alone unit for x-ray imaging.

4. The x-ray imaging system of claim 3, wherein said first wireless link communicates with a wireless controlled switch in said x-ray generator, said wireless controlled switch replacing a manually controlled switch in said stand alone unit that initiates x-ray generation.

5. The x-ray imaging system of claim 3 wherein said image controller further comprises a second wireless link that controls a wireless controlled switch that interrupts said x-ray generator in response to said x-ray exposure signal indicating that an exposure sufficient to provide a satisfactory image of said patient's teeth had been received.

6. The x-ray imaging system of claim 5 wherein said wireless controlled switch interrupts a power line that supplies power to an x-ray generating tube in said x-ray generator.

7. A method for retrofitting an existing x-ray generator having a first switch that is manually controlled to initiate a burst of x-rays, said method comprising:
    providing a digital x-ray controller that controls an imaging array configured to be positioned within a patient's mouth, said imaging array acquiring an image of said patient's teeth when said patient's head is illuminated with x-rays, said imaging array comprising an x-ray dosimeter that provides an x-ray exposure signal indicative of an x-ray exposure received by said imaging array;
    providing an image controller that is coupled to said imaging array and receives said x-ray exposure signal, said image controller comprising a first wireless link that controls said x-ray generator by initiating a pre-programmed x-ray exposure;
    replacing said first switch with a first wireless controllable switch that is actuated by said image controller to initiate said burst of x-rays and introducing a second wireless controllable switch into said x-ray generator at a location that interrupts the generation of x-rays by said x-ray generator, said image controller interrupting an x-ray exposure in response to said x-ray exposure signal indicating that an exposure sufficient to provide a satisfactory image of said patient's teeth had been received.

8. The method of claim 7 wherein said second wireless controllable switch interrupts a power line that supplies power to an x-ray generating tube in said x-ray generator.

\* \* \* \* \*